US012582749B2

(12) United States Patent
Ganey et al.

(10) Patent No.: US 12,582,749 B2
(45) Date of Patent: Mar. 24, 2026

(54) MENISCUS TEAR REPAIR SLING DEVICE

(71) Applicant: Vivex Biologics Group, Inc., Atlanta, GA (US)

(72) Inventors: Timothy Ganey, Tampa, FL (US); Paul Saluan, Westlake, OH (US)

(73) Assignee: Vivex Biologics Group, Inc., Atlanta, GA (US)

( * ) Notice: Subject to any disclaimer, the term of this patent is extended or adjusted under 35 U.S.C. 154(b) by 269 days.

(21) Appl. No.: 17/568,148

(22) Filed: Jan. 4, 2022

(65) Prior Publication Data

US 2022/0211909 A1 Jul. 7, 2022

Related U.S. Application Data

(60) Provisional application No. 63/133,606, filed on Jan. 4, 2021.

(51) Int. Cl.
| | |
|---|---|
| *A61F 2/30* | (2006.01) |
| *A61F 2/46* | (2006.01) |
| *A61L 27/36* | (2006.01) |
| *A61L 27/54* | (2006.01) |

(52) U.S. Cl.
CPC ...... *A61L 27/3654* (2013.01); *A61F 2/30756* (2013.01); *A61F 2/4618* (2013.01); *A61L 27/3604* (2013.01); *A61L 27/54* (2013.01); *A61F 2002/30757* (2013.01); *A61L 2300/414* (2013.01); *A61L 2430/06* (2013.01)

(58) Field of Classification Search
CPC ........ A61B 17/0469; A61B 2017/0646; A61L 27/3654; A61L 27/3604; A61L 27/54; A61L 2300/414; A61L 2430/06; A61F 2/4618; A61F 2002/30757; A61F 2002/30761; A61F 2/30756; A61F 2/3872; A61F 5/37
See application file for complete search history.

(56) References Cited

U.S. PATENT DOCUMENTS

| | | | |
|---|---|---|---|
| 5,061,283 A | 10/1991 | Silvestrini | |
| 5,723,008 A | 3/1998 | Gordon | |
| 7,871,440 B2 | 1/2011 | Schwartz et al. | |
| 7,998,204 B2 * | 8/2011 | Stone .................... | A61L 31/129 |
| | | | 623/13.18 |
| 8,006,700 B2 | 8/2011 | Demopulos et al. | |

(Continued)

FOREIGN PATENT DOCUMENTS

| | | |
|---|---|---|
| CN | 102716515 | 1/2014 |
| WO | 2015016761 | 2/2015 |

*Primary Examiner* — Megan Y Wolf
(74) *Attorney, Agent, or Firm* — Kilpatrick Townsend & Stockton LLP

(57) ABSTRACT

A meniscus tear repair sling device has a collagen membrane having a first end portion and a second end portion. The first end portion is configured to pass under a tear in a meniscus and wrap over and above the tear and extend past the meniscus and overlay the second end portion thereby enveloping a portion of the meniscus with a tear and forming the sling device. The first end portion and the second end portion form exposed overlying tails extending external of a knee joint. The tails are configured to be affixed to a portion of a tibia. The tails when tensioned close the tear by providing a lateral strain on the torn meniscus when the tails are affixed to a tibia adjacent the knee joint.

9 Claims, 5 Drawing Sheets

(56) References Cited

U.S. PATENT DOCUMENTS

| | | | |
|---|---|---|---|
| 8,084,428 B2 | 12/2011 | Spector et al. | |
| 8,092,529 B2 * | 1/2012 | Malaviya | A61B 17/0642 |
| | | | 623/23.72 |
| 8,409,250 B2 | 4/2013 | Schmieding et al. | |
| 8,814,903 B2 | 8/2014 | Sengun et al. | |
| RE45,895 E | 2/2016 | Michelson | |
| 9,314,234 B2 | 4/2016 | Hirotsuka | |
| 9,421,304 B2 | 8/2016 | Shortkroff et al. | |
| 9,492,592 B2 | 11/2016 | Hedman | |
| 9,675,643 B2 | 6/2017 | Weston et al. | |
| 9,687,511 B2 | 6/2017 | Weston et al. | |
| 9,724,088 B2 | 8/2017 | Domingo | |
| 9,831,354 B2 | 11/2017 | Li | |
| 10,251,639 B1 | 4/2019 | Yamada | |
| 10,265,438 B1 * | 4/2019 | Brahm | A61L 27/3662 |
| 10,299,829 B2 | 5/2019 | Yamada | |
| 10,413,572 B2 | 9/2019 | Namin et al. | |
| 10,433,830 B2 | 10/2019 | Sengun et al. | |
| RE47,722 E | 11/2019 | Michelson | |
| 10,645,921 B2 | 5/2020 | Temple et al. | |
| 2004/0267277 A1 * | 12/2004 | Zannis | A61F 2/4618 |
| | | | 606/86 R |
| 2007/0116682 A1 | 5/2007 | Atala et al. | |
| 2007/0156174 A1 * | 7/2007 | Kaiser | A61B 17/0642 |
| | | | 606/215 |
| 2010/0228335 A1 | 9/2010 | Schorgl | |
| 2011/0059178 A1 * | 3/2011 | Semler | A61L 27/3834 |
| | | | 424/548 |
| 2013/0030542 A1 * | 1/2013 | Grotz | A61B 17/0642 |
| | | | 623/20.35 |
| 2013/0344162 A1 | 12/2013 | Morse | |
| 2015/0224147 A1 * | 8/2015 | Tabet | A61K 35/50 |
| | | | 424/443 |
| 2016/0158291 A1 | 6/2016 | Kreke | |
| 2017/0020927 A1 * | 1/2017 | Ganey | C12N 5/00 |
| 2017/0136071 A1 | 5/2017 | Danilkovitch et al. | |
| 2023/0301786 A1 * | 9/2023 | Thyden | A61F 2/3094 |

* cited by examiner

MENISCUS TEAR REPAIR SLING DEVICE

Related Applications

The present application claims benefit from U.S. Provisional Application No. 63/133,606, filed Jan. 4, 2021 which is hereby incorporated by reference in its entirety.

TECHNICAL FIELD

This invention relates to a meniscus tear repair method and device.

BACKGROUND OF THE INVENTION

Most meniscus repairs involve tears. The most typical procedures rely on suturing the meniscus to close the tear opening. All these techniques require penetrating the damaged meniscus. In some cases, the suturing employs wire or filaments that cut into the meniscus causing additional damage. Many patents on suturing techniques to improve the repair techniques have been issued.

In some cases, as in U.S. Pat. No. 9,492,592 B2, a patch is laid over the tear and then sutured to the meniscus. U.S. Pat. No. 9,492,592 B2 employs a patch with crosslinking agents or reagents to accelerate tissue repair. The patch lays on the meniscus and is sutured to the meniscus or otherwise held thereto. U.S. Pat. No. 9,421,304 employs a double structure tissue system. In CN 102716515 (B) a biologic material and method is taught. The acellular matrix membrane on the inner layer, a porous structure collagen matrix member on a middle layer and a cell layer of cartilage cells on an outer layer. U.S. Pat. No. 5,084,428 B2 uses two sheets of collagen membranes, one above the tear, one below the tear, the two being attached together using sutures passing through the meniscus. U.S. Pat. No. 7,871,440 B2 has a unitary device for repairing such tears. The unitary device made of stomach lining that can wrap about the meniscus in some embodiments and is sutured to the soft tissue of the meniscus.

In all cases, the meniscus is exposed to suture penetration which in many cases creates additional micro tears and damage. Ideally, the repair of a tear in the meniscus should avoid creating additional damage and be configured to accelerate healing as an objective.

This objective is achieved by the present invention as described herein.

SUMMARY OF THE INVENTION

A meniscus tear repair sling device has a collagen membrane having a first end portion and a second end portion. The first end portion is configured to pass under a tear in a meniscus and wrap over and above the tear and extend past the meniscus and overlay the second end portion thereby enveloping a portion of the meniscus with a tear and forming the sling device. The first end portion and the second end portion form exposed overlying tails extending external of a knee joint. The tails are configured to be affixed to a portion of a tibia. The tails when tensioned close the tear by providing a lateral strain on the torn meniscus when the tails are affixed to a tibia adjacent the knee joint.

The sling device is configured to be placed in a cannula for delivery and implantation using a minimally invasive intraarticular and interarticular arthroscopic placement of the sling device to wrap over and under the meniscal tear and thereafter tensioned to provide lateral strain to close the tear prior to fixing the first and second end portion external of the meniscus.

The collagen membrane includes one or more of an amniotic membrane, a placental tissue membrane, an umbilical cord membrane, a laminated or stacked multilayer membrane. The collagen membrane has an inner surface and an outer surface, the inner surface being bioenhanced treated with biologic materials and growth factors to accelerate healing of the tear. The biologic materials and growth factors include organic compounds such as amino acids, purines, pyrimidines, vitamins, hyaluronic acid, acellular biologic material including non-cellular fractions and components as well as cellular components, and amniotic fluid.

The meniscus tear repair sling device further can have a cryoprotectant, wherein the collagen membrane is protected by the cryoprotectant. The collagen membrane with or without the cryoprotectant is cryolyophilized for storage as a freeze-dried sling device and the freeze-dried sling device is soaked in a liquid to render the sling device suitable for implantation.

A method of performing a meniscus tear repair comprises the steps of: providing a collagen membrane having a first end portion and a second end portion, the first end portion configured to pass under a tear in a meniscus and wrap over and above the tear and extend past the meniscus and overlay the second end portion thereby forming the sling device wherein the first end portion and the second end portion form exposed overlying tails extending external of a knee joint, the tails when tensioned close the tear by providing a lateral strain on the torn meniscus when affixed to a tibia adjacent the knee joint; inserting the device inside a cannula, the device being rolled to form a cylindrical shape sized to fit inside the cannula; inserting the cannula into the knee joint in delivering the device to wrap over and under the meniscal tear; pulling the device at the first end to slide the device into position and leaving the first end and second end exposed external the knee joint; and tensioning the device to create a lateral strain and fixing the tails to the tibia creating an intraarticular and interarticular extracapsular fixation.

Definitions

As used herein and in the claims:

As used herein the device is provided as a one-piece repair device. Optional stabilization or fixation in addition to the sling repair device may be used by a surgeon if desired.

The biologic materials and growth factors include organic compounds such as amino acids, purines, pyrimidines, vitamins, hyaluronic acid, acellular biologic material including non-cellular fractions and components as well as cellular components, and amniotic fluid. Biologic materials may also include cells, bioactive agents, biologically derived agents, biological lubricants and biocompatible inorganic materials. It should be understood that the above materials are identified by way of example only, and the present invention is not limited to any particular material unless expressly called for in the claims.

BRIEF DESCRIPTION OF THE DRAWINGS

The invention will be described by way of example and with reference to the accompanying drawings in which.

DETAILED DESCRIPTION OF THE INVENTION

Figure 1:
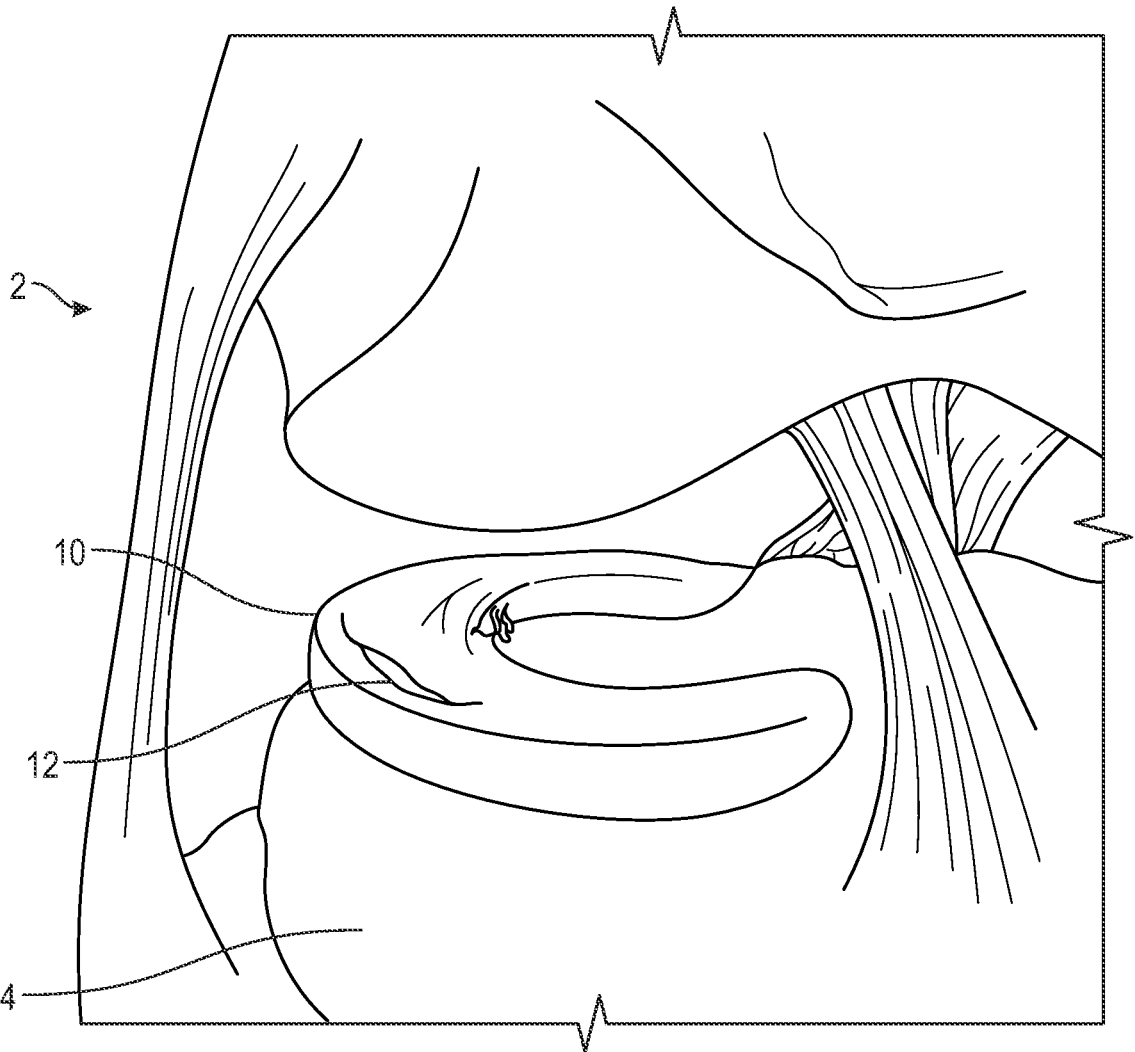
FIG. 1 is a perspective view of a portion of a knee joint exhibiting a typical torn meniscus having a right lateral tear

With reference to FIG. 1, a partial view of a knee joint is shown. The knee joint 2 has a meniscus 10 exhibiting a tear 12, this tear 12 is on the lateral side of the meniscus as illustrated. Only a portion of the knee joint is illustrated for purposes of demonstrating a typical tear in a meniscus.

The lateral tear 12 as shown in FIG. 1 is a typical and more common tear of a meniscus. Typical repairs involve suturing the tear 12 passing the suture through the meniscus 10 and drawing it tight. These types of repairs come with the risk of having the sutures cut into the soft tissue of the meniscus 10 creating additional damage if not careful. Numerous patents have been issued on trying to perfect ways to minimize the risk of further damage to the soft tissue. The current invention is illustrated in FIGS. 2-6 provides a unique solution to the problem of repairing a meniscus tear particularly a lateral tear 12.

Figure 2:
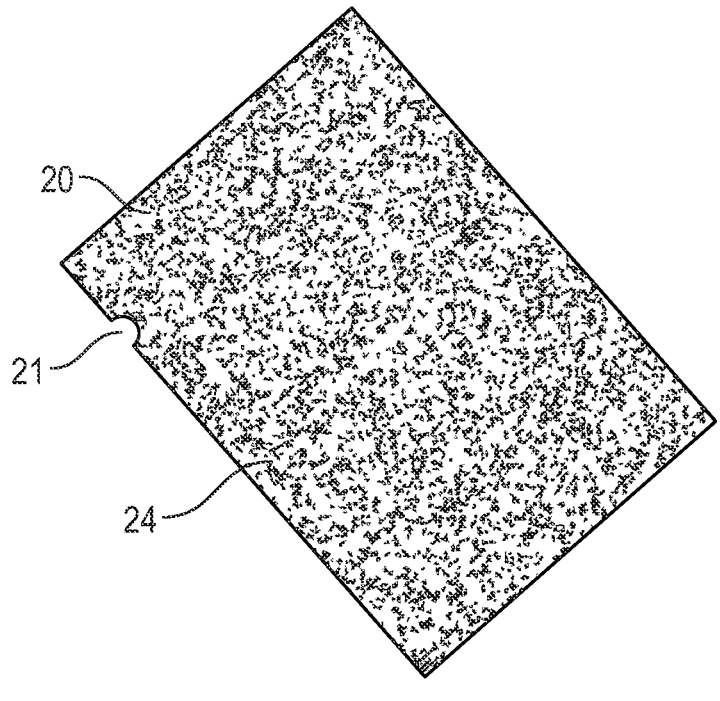
FIG. 2 is a perspective view of an exemplary meniscus tear sling device of the present invention shown in a flat rectangular shape in a dried or dehydrated condition.

With reference to FIG. 2, a sling device 20 is illustrated. As shown, the device 20 is made as a collagen membrane formed as a flat sheet of biologic material, preferably composed of amniotic or placental tissue such that it can be dried and produced in a flat rectangular shape as illustrated. As shown, there is a notch 21 provided that establishes which surface the tissue has. As illustrated, the tissue has a first surface 24 and a second surface 22 as shown. The first surface 24 will lie against the meniscus 10 tissue. This surface 24 can be treated with numerous biological agents and or growth factors to stimulate tissue repair as will be discussed later.

Figure 3:
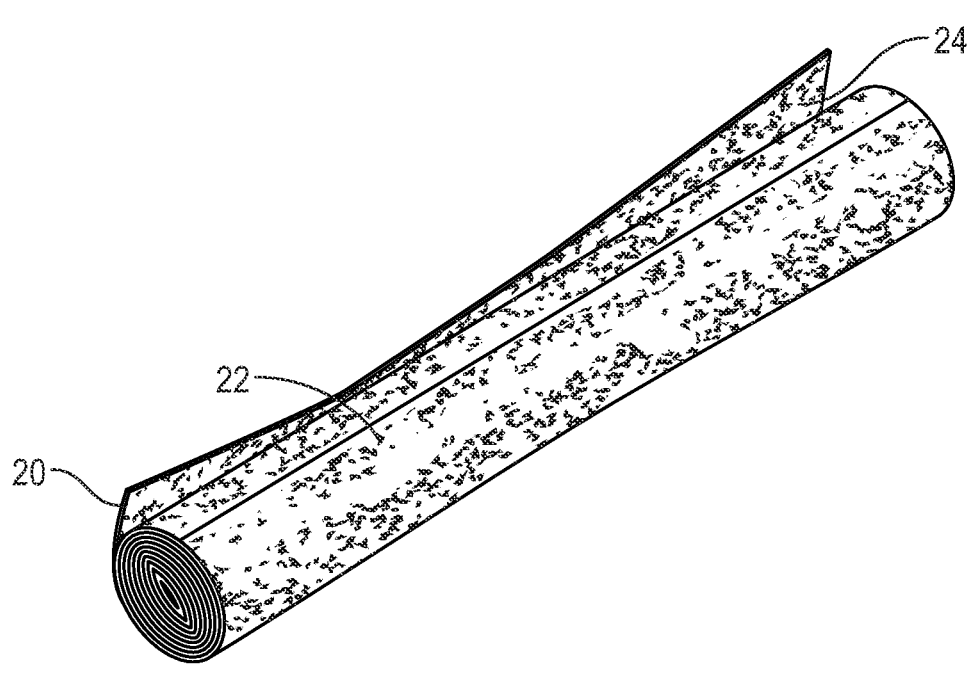
FIG. 3 is a perspective view of the sling device of FIG. 2 after hydration shown rolled into a cylindrical shape for placement in a cannula.
Figure 4:
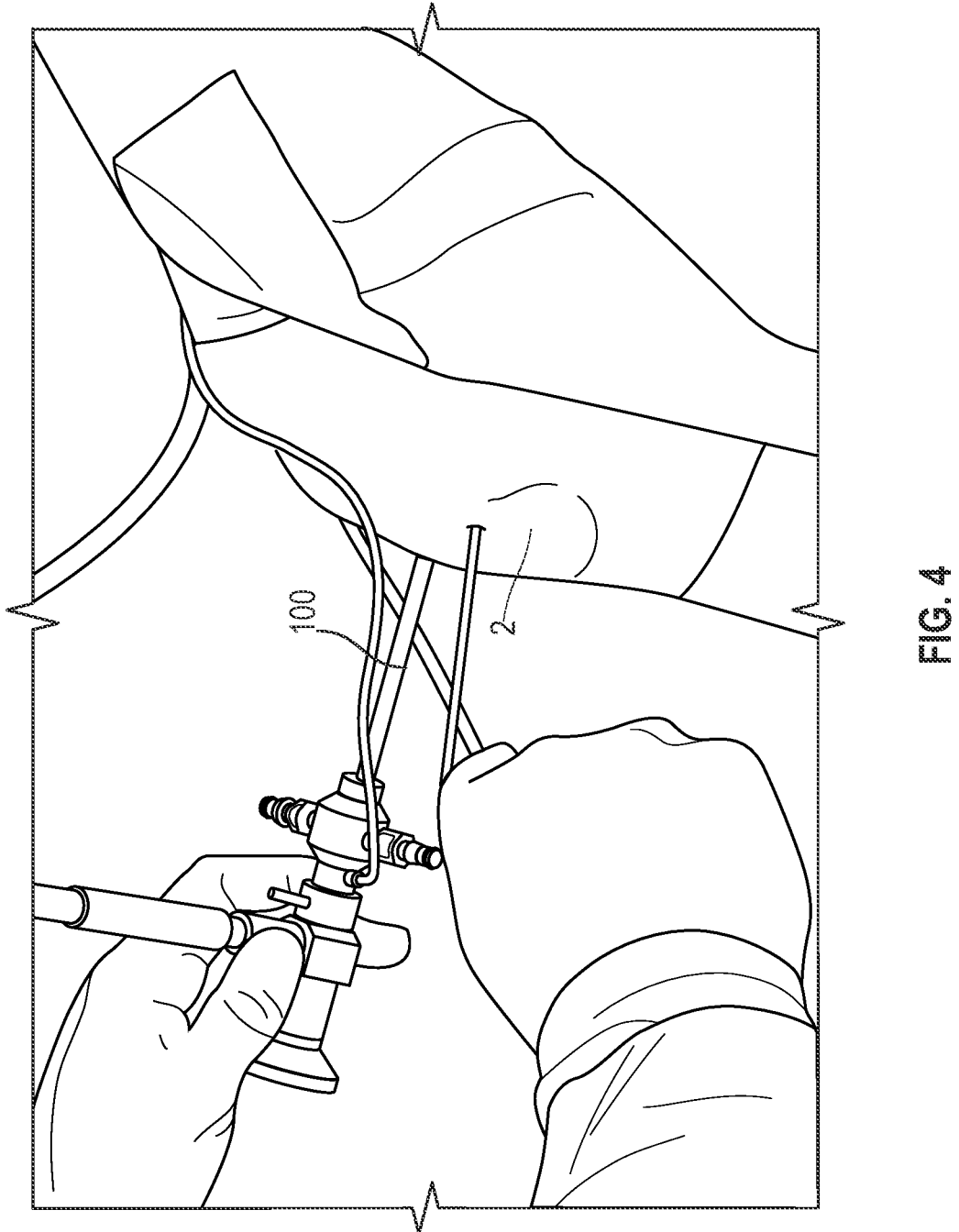
FIG. 4 is a representative photo of a surgeon arthroscopically inserting a cannula with the sling device into a knee joint with a torn meniscus to be repaired.
Figure 5:
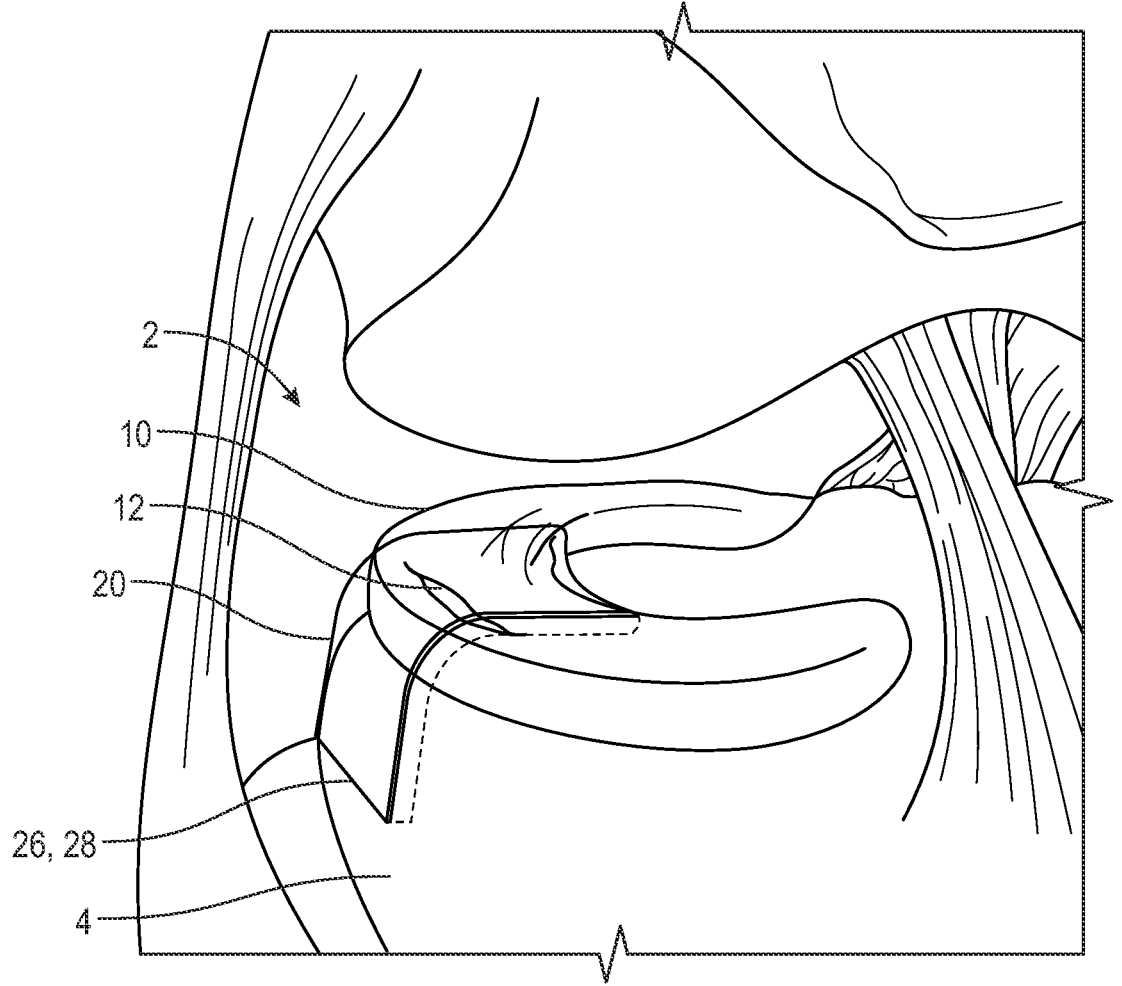
FIG. 5 is a perspective view of the sling device positioned enveloping the torn meniscus.

With reference to FIG. 3, one of the ideal placements of this sling device 20 is to configure it in such a way that the dehydrated tissue membrane can be rehydrated and rolled into a cylindrical tube sized to fit inside a cannula. As illustrated in FIG. 4, the ideal placement of the sling device 20 is achieved using an arthroscopic procedure with instruments 100 that provides a cannula that is inserted into the knee joint 2 and delivers the rolled membrane 20 into the knee joint 2. The rolled sling device 20 can then be unfurled under the meniscus 10 and an end delivered under the meniscus 10, then up and over the meniscus 10 to cover the tear 12, as illustrated in FIG. 5. Alternatively, the device 20 could be delivered over the top of the meniscus 10 and then under the meniscus 10 and out achieving the same result as illustrated in FIG. 5. Regardless of the approach, the sling device 20 envelopes the torn meniscus 10 lying directly over and under the tear 12 in such a fashion that the first or inner surface 24 laden with the bioenhanced agents is placed against the tear 12. The tear 12 is closed by tensioning the tails 26 and 28 of the sling device 20. These tails 26, 28 extend outward of the knee joint and can be affixed to the tibia 4 as shown in FIG. 5. The fixing to the bone 4 provides a secure placement of the sling device 20 and ensures that a slight lateral outward tension is placed on the meniscus 10 that keeps the tear 12 closed to accelerate the healing process.

Figure 6:
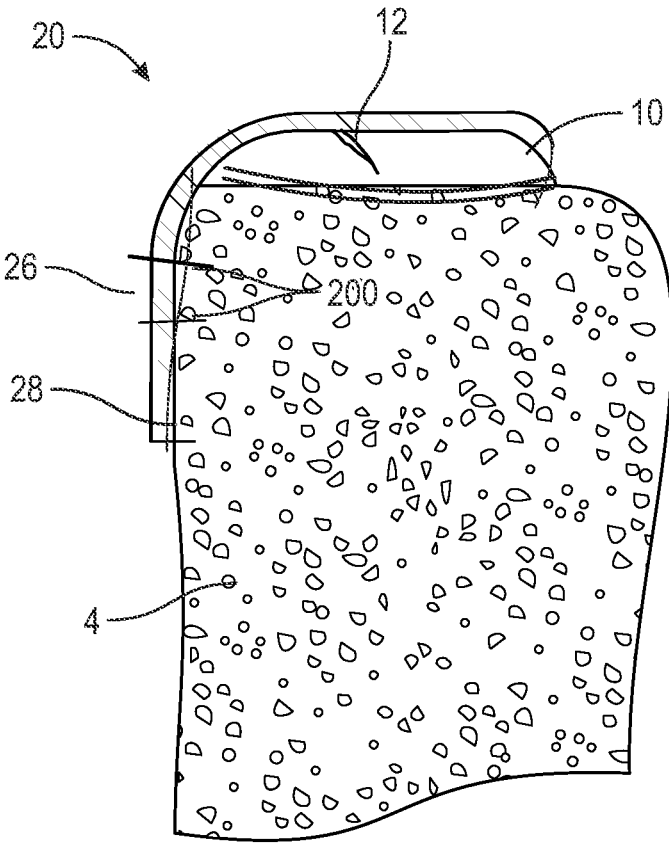
FIG. 6 is a cross-sectional view of the sling device enveloping the torn meniscus taken from FIG. 5.

This is further illustrated in FIG. 6 wherein the tear is shown as element 12 of the meniscus 10 and the sling device 20 is shown enveloping the entire lateral portion of the meniscus 10. As further illustrated in FIG. 6, the tails 26, 28 can be affixed or sutured to the tibia bone 4 using sutures 200 or anchors to provide the necessary tension.

As noted, the collagen membrane first surface 24 can be bio actively enhanced with various growth factors or biologic materials to accelerate healing of the meniscus tear 12.

One aspect of the invention uses hyaluronic acid (HA) from reptilian sources or rooster combs. The principal characteristics of HA is its ability to retain water. This contributes significantly to the skin maintaining a youthful appearance. The levels of HA in the body decreases with each passing year. As the levels decrease, it adversely impacts the skin's ability to retain moisture, thus leading to inevitable wrinkles. In one aspect of the invention, the use of alligator derived hyaluronic acid supports healthy regenerative tissue function. Hyaluronic acid helps reproduce healthy cells within a collagen matrix by increasing hydration and acting as a lubricant among the collagen matrix of the device. Hyaluronic acid is an element of the tissue's construction and weakens with age, the HA supplements with collagen help ensure ample levels stay in the tissue to sustain its overall function. Accordingly, the benefits of hyaluronic acid are becoming increasingly used an effective anti-aging care treatment in the soft tissue industry. This composition employing a reptilian source greatly enhances this benefit.

In one aspect of the invention, a purified source of amniotic fluid similar to or the same as described in U.S. Pat. No. 10,413,572 issued on Sep. 17, 2019 is combined with hyaluronic acid derived from alligator deep derma fascia is formed into an injectable that can be applied as a coating on the first surface 24. The teachings of U.S. Pat. No. 10,413, 572 are being incorporated by reference in its entirety herein. An important aspect of this combination is the HA is an anti-inflammatory which when combined with the amnion fluid is ideal for treating tears and pain associated with arthritis, sore joints and muscle and meniscus injuries. The built-in growth factors in the amnion are tissue regenerative and therefore the combination improves the performance of both.

The composition is particularly useful when the hyaluronic acid derived form an alligator source is combined with bone regenerative materials such as bone particles, bone fibers, mineralized, demineralized, or combinations thereof. The exposure of the HA molecules is supportive of osteoinductivity. Accordingly, such combinations are very useful. In most advanced materials, biologic compositions with or without stem cells can be combined to form the composition. By way of example, materials found in both U.S. Pat. No. 9,675,643 "Biologic Composition and Method of Manufacture" and U.S. Pat. No. 9,687,511 "Acellular Biologic Composition and Method of Manufacture", which are being incorporated by reference in their entirety herein, can be combined with HA to create a repair material with improved properties when applied to the first surface 24.

Similarly, the composition can be ideally used in procedures for repairing damaged discs. For way of example, the HA molecules derived from alligators can be combined with nucleus pulposus in a dry powdered form as to create a composition ideally suited for repairing damaged spinal discs. The nucleus pulposus is fully described in U.S. Pat. No. 10,064,896 entitled, "Spinal Disc Regenerative Composition and Method of Manufacture and Use" which is being incorporated by reference herein in its entirety. This use of nucleus pulposus is complimentary to meniscus tissue regeneration or tear repair.

In yet another embodiment, the disc repair composition may include stem cells in combination with HA molecules. In U.S. Pat. No. 10,645,921 issuing May 12, 2020 entitled, "Viable Disc Regenerative Composition and Method of Manufacture and Use" which is being incorporated by reference in its entirety, the composition has HA molecules combined with dehydrated micronized nucleus pulposus and bone marrow derived mixture of components, including non-whole cellular components in a biologically compatible, polyampholyte protectant or cryoprotectant. This use of the composition would be similarly protected by the polyampholyte which creates an improved protection of the HA molecules from damage when stored for later use in the repair of meniscus tears.

As can be seen, the use of the alligator derived HA molecules is not only compatible, but ideally suited for these compositions in a variety of treatments. New advancements have been found wherein exosomes and other acellular biological components can be made into freeze-dried compositions as is taught in co-pending patent application U.S. Ser. No. 16/710,472 entitled "Exosome Composition and Method of Manufacture" and others.

The inventors believe all these new discoveries can be effectively used in combination with the HA molecules derived from alligators without adverse effects.

Various additional benefits of HA of the present invention include: Neutral exothermic foaming, Water structuring, hydrogel capacity, Osteoconductive, Bone-like Geometric Properties, Porosity, Connectivity, Modeling, Non-toxic; Compatible pH, isotonic, non-hemolytic, Negative charge of matrix exceeding that of rooster comb or bacterial expression, Non-hemolytic, isotonic, Aqueous binder of calcium phosphates, hydroxyapatites, open foamed graft extenders, Hybrid composition with bone allografts; i.e. DBM fibers and micronized matrices, Dermal matrices; micronized, fenestrated and compressed, shaped and stamp formed in sheets, suitable for die-cutting and Evolving tension from retraction and modeling of pores, Fiber tension across pores to sustain superstructure, Osteogenesis—bone formation response to tensile forces and stretching, Osteogenesis requires a tension-dependent mechanical cue, Foams of varying sized areas display variations in surface curvature, As matrix surrounding pores dissolves, the internal surface expands in relationship to the pore radius based on a well formulated Surface Area=3.14 (pi)×4×r2, Increasing connectivity based on optimal bone formation from 250-micron through 750-micron porosity, Integrating solid based on open foam consolidation, Bone forms and models to shear; integrating aspects and assets of both tensile and compressive combination Creating differential particle thickness and laminar distribution is also a benefit. Regarding bone, the partially demineralized tissue will be more osteogenic than the less "revealed" particles. If these are also the larger, then the surface area of the larger is exponential to the change in diameter of the particle. If the size is then exposed to stratification, or lamination, or plying, then the larger particles with more surface area are at the bottom. If the HA incorporation allows a strip on the posterior lamina/gutter for fusion, then the greater release of growth factors is near the bone, and a grade percentage of less potential more near the soft tissue surfaces. The benefit is getting bone directed regeneration mesially, and more lateral or peripheral regenerating to the soft tissues supporting them is ideally suited for meniscus tear repair. In those aspects, the second surface 22 can be coated to enhance the bone regeneration on this treated secondary outer surface 22.

HA also incorporates differential buoyance and microcortical variability. The inherent variability in the 100 to 300 micron range for use with materials of many tissue types, such as cartilage, bone, dermis, meniscus and spinal cord. Assuming a regular distribution of particles produced by the manufacturing, the significant portion will be in the 200-225 um range. The invention takes advantage of the difference in size as a discriminating means of separating and laminating an allogeneic tissue construct. The size of particles can be designed to define a differential stack of matrix where size becomes an extension of angular velocity. Changing radius, speed, and collection allow drying and permit the collection of particles in colloids such as hyaluronic acid. Separating by size can be achieved by vibrational separation during polymerization. Size-varying would be between 100-300 micron. Base vibration tuned to the sizing of the particles. Screen could be solid as to transmit vibrational alone. Screen could be active sieve to drop materials into standing HA polymerization to separate.

With reference to the present invention, in one aspect of the invention, the first surface 24 can be coated with a composition of exosomes derived from a tissue source, the composition can be freeze-dried and stored at ambient conditions or frozen for storage. Preferably, in either condition, the exosomes are intermixed with a cryoprotectant that is non-DMSO based, preferably a carboxylated ε-poly-1-lysine cryoprotectant.

While it is understood the exosome composition can be derived from any number of tissue sources, such a muscle, fat, organs or bone or bone marrow, the representative examples and test data are based on exosomes derived from bone marrow from a cadaver donor.

The composition is directed to achieving a concentration of exosomes from the source tissue. The source tissues have been markedly similar to those wherein successful harvesting of stem cells has been accomplished. These include, by way of example, placental tissues, bone marrow, umbilical cords, whole blood, and fat. The harvesting of exosomes yields compositions rich in concentrations of exosomes, typically concentrations are 1E6 to 1E10 per ml. It has further been determined that these concentrations of exosomes can be combined with other materials to facilitate delivery and use in medical procedures. By way of example, kits with the concentrated exosome composition when made having other vials or containers of bone particles or bone fibers that are mineralized or demineralized which are mixed to form an exosome laden bone blend for use in bone repair. Similarly, the concentrated exosome concentration having separate vials of nucleus pulposus particles provided as a kit when mixed together yield a regenerative spinal disc or meniscus tear repair composition. Kits of vials of cartilage material or other soft tissue provide unique combinations when Mixed with the concentrated exosomes that are particular useful in repairing such tissue tears such as knee injuries and Achilles tendon tears, particularly so when the tear is only partial. These uses are in no way intended to be limiting, but rather exemplary of a wide range of uses either singularly or combined with other tissue types in the form of a kit. One particularly useful combination is a concentration of exosomes loaded in a bone gel and applied as a coating on the first surface 24. Bone gels can be in the form of a moldable gel or paste or can be a cohesive blend of gel and bone particles and are available in a range of types perfectly suited to be loaded with a concentration of exosomes. This combination ensures the exosomes are delivered directly to the repair site. As noted, these combinations yield a remarkable performance gain in remodeling and regenerating damaged tissue. Fabrication of a variety of types include molding, forming, drying, centrifugal casting, cryo-lyophilization and use at varying dehydrated states and carrier combinations to sustain malleability and to print in additive investments of specific shape and volume, commonly called 3D printing. all of which can be used with the compositions of exosomes and biocompatible cryoprotectant. This is particularly convenient in the dehydrated or freeze-dried condition wherein the composition can be built into bioabsorbable carriers such as the sling device allowing for a concentration of exosomes to be effectively time released.

With reference to certain embodiments of the present invention which is a tissue regenerative biological composition made from bone marrow, it is believed best understood by the methods used to process and recover the biological composition as is taught in co-pending application U.S. Ser. No. 16/710,472 incorporated herein by reference in its entirety.

By adding growth factors or biological compositions to the collagen membrane, whether on the first surface 24 alone or the second surface 22 or both with the same or different coatings, improved healing and repair can be achieved. This feature allows the sling device 20 to be tailored to achieve specific repair potentials dependent on the patient's condition and tissue conformation.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described, which will be within the full intended scope of the invention as defined by the following appended claims.

What is claimed is:

1. A method of performing a meniscus tear repair, comprising:
providing a collagen membrane having a first end portion and a second end portion, wherein the collagen membrane comprises one or more of an amniotic membrane, a placental tissue membrane, and an umbilical cord membrane; wherein the first end portion is configured to pass under a tear in a meniscus and wrap over and above the tear and extend past the meniscus and overlay the second end portion, thereby forming a sling device wherein the first end portion and the second end portion form exposed overlying tails extending externally from a knee joint, the tails, when tensioned, close the tear by providing a lateral strain on the torn meniscus when affixed to a tibia adjacent the knee joint;
inserting the device inside a cannula, the device being rolled to form a cylindrical shape sized to fit inside the cannula;
inserting the cannula into the knee joint, delivering the device to wrap over and under the meniscal tear;
pulling the device at the first end portion to slide the device into position and leaving the first end portion and second end portion exposed external to the knee joint; and
tensioning the device to create a lateral strain and fixing the tails to the tibia, creating an intraarticular and interarticular extracapsular fixation, wherein the meniscus is not exposed to suture penetration.

2. The method of claim 1, wherein the collagen membrane comprises an inner surface and an outer surface, wherein the inner surface comprises biologic materials and growth factors to accelerate healing of the tear.

3. The method of claim 2, wherein the biologic materials and growth factors are selected from a group consisting of amino acids, purines, pyrimidines, vitamins, hyaluronic acid, acellular biologic material, amniotic fluid, and combinations thereof.

4. The method of claim 2, wherein the biologic materials comprise non-whole cellular components.

5. The method of claim 2, wherein the inner surface comprises exosomes.

6. The method of claim 1, wherein the collagen membrane comprises a polyampholyte protectant or cryoprotectant.

7. The method of claim 6, wherein the cryoprotectant comprises ε-poly-1-lysine.

8. The method of claim 6, wherein the collagen membrane is cryolyophilized, stored, and soaked in a liquid prior to use of the collagen membrane in the meniscus tear repair.

9. The method of claim 1, wherein the collagen membrane is cryolyophilized, stored, and soaked in a liquid prior to use of the collagen membrane in the meniscus tear repair.

* * * * *